United States Patent [19]

Yang

[11] Patent Number: 5,420,213
[45] Date of Patent: May 30, 1995

[54] POLYSILOXANES, METHODS OF MAKING SAME AND HIGH REFRACTIVE INDEX SILICONES MADE FROM SAME

[75] Inventor: Shih-Liang S. Yang, Laguna Hills, Calif.

[73] Assignee: Allergan, Inc., Irvine, Calif.

[21] Appl. No.: 226,223

[22] Filed: Apr. 11, 1994

Related U.S. Application Data

[60] Continuation of Ser. No. 48,092, Apr. 15, 1993, abandoned, which is a division of Ser. No. 868,412, Apr. 14, 1992, Pat. No. 5,233,007.

[51] Int. Cl.$^6$ ............... C08F 283/12; G02C 7/02; G02C 7/04
[52] U.S. Cl. .................. 525/478; 528/15; 528/25; 528/31; 528/37; 528/43; 351/159; 351/160 R; 523/107
[58] Field of Search ............ 528/37, 31, 43, 15, 528/25; 525/478; 351/159, 160 R

[56] References Cited

U.S. PATENT DOCUMENTS

| | | | |
|---|---|---|---|
| 3,088,964 | 5/1963 | Ryan | 260/448.2 |
| 3,284,406 | 11/1966 | Nelson | 260/46.5 |
| 3,341,490 | 9/1967 | Burdick | 260/37 |
| 3,457,214 | 7/1969 | Modic | 260/37 |
| 3,479,320 | 11/1969 | Bostick | 528/37 |
| 3,686,254 | 8/1972 | Morehouse | 528/37 |
| 3,992,355 | 11/1976 | Itoh et al. | 106/287 |
| 3,996,187 | 12/1976 | Travnicek | 260/375 B |
| 3,996,189 | 12/1976 | Travnicek | 260/375 B |
| 4,247,674 | 1/1981 | Koshar et al. | 528/21 |
| 4,380,643 | 4/1983 | Yoshida et al. | 548/260 |
| 4,418,165 | 11/1983 | Polmanteer et al. | 523/210 |
| 4,535,141 | 8/1985 | Kroupa | 528/15 |
| 4,573,998 | 3/1986 | Mazzocco | 623/6 |
| 4,615,702 | 10/1986 | Koziol et al. | 623/6 |
| 4,618,665 | 10/1986 | Braun et al. | 528/25 |
| 4,647,282 | 3/1987 | Fedorov et al. | 623/4 |
| 4,737,558 | 4/1988 | Falcetta et al. | 526/279 |
| 4,778,860 | 10/1988 | Morita et al. | 525/431 |
| 4,785,047 | 11/1988 | Jensen | 524/714 |
| 4,868,151 | 9/1989 | Reich et al. | 525/479 |
| 4,882,398 | 11/1989 | Mbah | 525/478 |
| 5,006,580 | 4/1991 | Kasuya et al. | 524/264 |

FOREIGN PATENT DOCUMENTS 1273144  8/1990  Canada .

(List continued on next page.)

OTHER PUBLICATIONS

Gollmar, Preparation of Some Unsaturated Silanes, Journal of Polymer Science Part A1, vol. 9, No. 2, Feb. 1971, pp. 571–574.

(List continued on next page.)

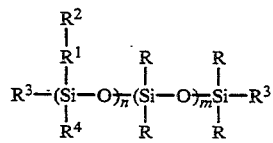

wherein each R and $R^4$ is independently selected from alkyl radicals, substituted alkyl radicals, aryl radicals and substituted aryl radicals; each $R^1$ is independently selected from divalent radicals; each $R^2$ is independently selected from aryl radicals and substituted aryl radicals; each $R^3$ is independently selected from monovalent hydrocarbon radicals having a multiple bond and monovalent substituted hydrocarbon radicals having a multiple bond; n is an integer in the range of about 6 to about 500; and m is an integer in the range of 0 to about 500. Methods for making such polysiloxanes are also disclosed. In addition, high refractive index, that is having a refractive index of at least about 1.46, silicone compositions useful in the fabrication of lens bodies are disclosed.

18 Claims, No Drawings

FOREIGN PATENT DOCUMENTS 0110537   6/1984   European Pat. Off. .
0202542  11/1986   European Pat. Off. .
1235722   5/1960   France .
2446818   4/1975   Germany .

OTHER PUBLICATIONS

Saam, Formation of Linear Siloxane Polymers, 1990 American Chemical Society, pp. 71–89.

Fish et al, Ring Opening Polymerization of Cyclotetrasiloxanes with Large Substituents, pp. 36–37, Polymer Reprints, 31(1), Apr. 1990.

Boutevin et al, Synthesis of Fluorinated Polysiloxanes. 8. Properties at Low and High Temperatures of Polysiloxanes with Fluronated Graft Macromolecules, vol. 24, (3), pp.629–632 (Feb. 4, 1991).

Rasoul et al, Thermal and Rheological Properties of Alkyl-Substitute Polysiloxanes, 1990 American Chemical Society, pp. 91–96.

Zaph et al, Synthesis and Properties of New UV-Curable Silicones With High Refractive Index, Polymeric Prints 30(2), p. 107 (1989).

Grigoras et al, Conformational Analysis of Substituted Polysiloxane polymers, 1990 American Chemical Society, pp. 125–144.

Grigoras, Substituted Polysiloxane Polymers: Conformation of the Pendant Groups, Polymer Preprints 31(1), 697 (1990).

*Primary Examiner*—John C. Bleutge
*Assistant Examiner*—Margaret W. Glass
*Attorney, Agent, or Firm*—Frank J. Uxa, Jr.; Gordon L. Peterson

[57]   ABSTRACT

A new class of polysiloxanes is disclosed. Such polysiloxanes have the formula

POLYSILOXANES, METHODS OF MAKING SAME AND HIGH REFRACTIVE INDEX SILICONES MADE FROM SAME

This application is a continuation of application Ser. No. 08/048,092, filed Apr. 15, 1993, now abandoned, which, in turn, is a division of application Ser. No. 07/868,412, filed Apr. 14, 1992, now 5,233,007.

BACKGROUND OF THE INVENTION

The present invention relates to polysiloxanes, methods for producing such polysiloxanes and high refractive index silicone materials made from such polysiloxanes, for example, for use in intraocular lenses. More particularly, the invention relates to polysiloxanes which are structured and are produced to provide silicone materials which have an advantageous combination of properties, including a high refractive index, and are useful in intraocular lenses.

Intraocular lenses (IOLs) have been known for a long time. Such lenses are surgically implanted into the human eye to replace damaged or diseased lenses of the eye.

Whereas IOLs can be made from "hard" polymeric or glass optical materials, soft resilient polymeric materials comprising polysiloxane polymers or copolymers have been increasingly used in the art for this purpose.

IOLs made from silicone polymeric materials are preferably deformable, so that for implantation a smaller incision needs to be surgically cut in the eye than for the implantation of "hard" IOLs. In this respect, the size and mechanical characteristics of the silicone polymeric IOLs play an important role. As it will be well understood by those skilled in the art, for successful implantation the lens must have sufficient structural integrity, elasticity and elongation and small enough size to permit the folding for insertion through a small incision. After insertion, the lens must, of course, regain its original molded shape and have sufficient structural integrity to retain such shape under normal use conditions.

It will be further understood by those skilled in the art that the thinner is the lens, the easier is the surgical insertion procedure. On the other hand, in order to function as an IOL, the lens material must have sufficient optical refractory power. Consequently, the higher is the optical refractive index of the silicone material, the thinner can be the lens to obtain the same optical refractory power.

Some silicone polymeric materials described in the prior art contain a reinforcer distributed in the polymeric silicone resin. Usually such reinforcement of the silicone polymeric material is necessary for the polymeric material to attain adequate structural strength to be used as a foldable IOL. Examples of reinforced silicone resins suitable for use as soft contact lenses or IOLs are described in U.S. Pat. Nos. 3,996,187; 4,615,702; 3,996,189.

Travnicek U.S. Pat. No. 3,996,189 discloses that the inclusion of diphenyl siloxane or phenyl-methyl siloxane into a polysiloxane increases the refractive index of the polymer. However, using such phenyl-containing siloxanes as refractive index increasing components results in a polymer which has reduced flexibility or elongation. Thus, although the refractive index is advantageously increased, the elongation of the polymer (and the foldability of an IOL produced from such polymer) is disadvantageously decreased. It would be advantageous to provide a siloxane polymer with high refractive index and sufficient elongation to provide a foldable IOL.

Koziol et al U.S. Pat. No. 4,615,702 discloses IOLs made from silicone polymers obtained by polymerization of such monomers as octamethylcyclotetrasiloxane, octaphenylcyclotetrasiloxane, trimethyltriphenylcyclotrisiloxane, and divinyltetramethyldisiloxane. Although such IOLs may have high refractive indexes because of the relatively high concentrations of phenyl groups, they also disadvantageously have reduced elongation, as do the materials disclosed by Travnicek U.S. Pat. No. 3,996,189, noted above.

Canadian Patent 1,273,144 discloses the inclusion of refractive index modifying groups, such as phenyl groups, into hydride-containing siloxanes by reacting a portion of the hydride groups with carbon-carbon unsaturation bonded to the refractive index modifying group. After this reaction, the unreacted hydride groups of the modified hydride-containing siloxane are reacted with a compound having at least two carbon-carbon unsaturated bonds to form a cross-linked polysiloxane. This system is somewhat difficult to control and may not be suitable for mass production of silicone lenses because of potentially large batch-to-batch quality variations. For example, the refractive index modifying groups should be sufficiently numerous and evenly distributed in the hydride-containing siloxane to provide the desired refractive index without detrimentally affecting the other properties of the final polymer. At the same time, the unreacted hydride groups remaining on the siloxane must be sufficiently numerous and evenly distributed to provide for the desired cross-linking reaction. These factors can create a reaction control problem which may result in a final polymer not having the desired refractive index and/or not having one or more other desired physical properties. It would be advantageous to provide for increasing the refractive index of a polymer with little or no effect on the cross-linking of the final polymer.

Mbah U.S. Pat. No. 4,882,398 discloses the presence of up to about 40% by weight of a resinous organosiloxane copolymer consisting essentially of trimethyl siloxy, dimethyl vinyl siloxy and $SiO_2$ units in a diorgano vinyl siloxy-terminated polydiorgano siloxane containing at least 95 mole % of dimethyl siloxane units and having a viscosity greater than about 12 Pa.s at 25° C. decreases the viscosity of the mixture relative to the viscosity of the polydiorgano siloxane. Although this patent does disclose certain aryl and aralkyl groups attached or bonded to a siloxane, there is no teaching or suggestion of any effect on the refractive index of the final polymer as a result of the inclusion of the monovalent hydrocarbon radicals or monovalent halogenated hydrocarbon radicals. Also, the amount of these groups which is included is such as to have little or no effect on the refractive index of the final polymer.

SUMMARY OF THE INVENTION

New polysiloxanes, methods for making such polysiloxanes, cross-linked copolymers derived from such polysiloxanes, and lenses, for example, IOLs, made from such cross-linked copolymers have been discovered. The present polysiloxanes can be produced in a relatively easy and straight forward manner. The cross-linked copolymers derived from such polysiloxanes have a very advantageous combination of properties. In the past, a high content of phenyl groups in a siloxane elastomer, such as a polymethylphenyl siloxane, did increase the refractive index, but also disadvantageously drastically altered the other physical properties, such as elongation and modulus, of the material. The present invention takes advantage of aryl-containing groups to increase refractive index, while reducing or even eliminating the disadvantageous effects that the presence of phenyl groups has heretofore had on the properties of polysiloxane elastomeric compositions. Because these disadvantages are reduced or eliminated, an increased concentration of aryl-containing groups can be included, thus further enhancing the refractive index of the final elastomeric product. For example, cross-linked copolymers produced from the present polysiloxanes can provide optically clear compositions which have high refractive indexes, preferably about 1.46 and above, and are sufficiently flexible so that IOLs can be produced from such compositions which are foldable so as to be inserted into a human eye through a small surgical incision, for example on the order of about 3 mm.

The present polysiloxanes have the formula

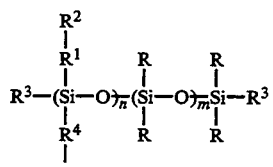

wherein each R and $R^4$ is independently selected from the group consisting of alkyl radicals, substituted alkyl radicals, aryl radicals and substituted aryl radicals; each $R^1$ is independently selected from the group consisting of divalent radicals; each $R^2$ is independently selected from aryl radicals and substituted aryl radicals; each $R^3$ is independently selected from the group consisting of monovalent hydrocarbon radicals having a multiple bond and substituted monovalent hydrocarbon radicals having a multiple bond; n is an integer in the range of about 6 to about 500; and m is an integer in the range of 0 to about 500.

Compositions, for example, elastomeric compositions, in accordance with the present invention comprise a cross-linked copolymer of at least one of the above-noted polysiloxanes and at least one cross-linker component, for example, a poly organo hydrogen siloxane. Such compositions, which preferably further comprise at least one reinforcer component in an amount effective to increase the strength of the composition, are preferably optically clear and have a refractive index of at least about 1.46. Such compositions may be used to produce lens bodies, for example, optics for IOLs, for use in or on a mammalian eye.

Methods for making polysiloxanes, such as the polysiloxanes described above, are also disclosed. Such methods take advantage of cyclic hydride-containing siloxane monomers, a number of which are commercially available, as starting materials. These cyclic siloxane monomers have well defined compositions so that the concentration of aryl-containing groups substituted for the hydride groups can be easily and very effectively controlled, resulting in polysiloxanes having effectively controlled and distributed aryl-containing substituents.

DETAILED DESCRIPTION OF THE INVENTION

The present polysiloxanes have the formula as described above. The amount of aryl-containing substituents in such polysiloxanes is preferably controlled to provide a polysiloxane and/or a cross-linked elastomeric composition derived from such polysiloxane with the desired refractive index, preferably at least about 1.46, more preferably at least about 1.48 and still more preferably at least about 1.50. The aryl-containing substituents preferably are present in such polysiloxanes in an amount of at least about 10 mol %, more preferably at least about 15 mol % and still more preferably at least about 20 mol %, of the total silicon-bound substituents in such polysiloxane. The aryl-containing substituents may be as much as about 40 mol % or about 50 mol % or more of the total silicon-bound substituents in such polysiloxane. In one particularly useful embodiment, substantially all of the aryl-containing substituents are the $-R_1-R_2$ groups. In this embodiment, each $R^4$, and more preferably each R and $R^4$, is independently selected from alkyl radicals and substituted alkyl radicals. Still more preferably, each $R^4$ and R is methyl.

Among the alkyl radicals useful in the present polysiloxanes are those which include 1 to about 10 carbon atoms, preferably 1 to about 4 carbon atoms. Examples include methyl, ethyl, propyl, butyl, octyl and decyl. These alkyl radicals may be substituted with substantially non-interfering substituents which have no substantial detrimental effect on the resulting polysiloxane or on the elastomeric composition produced from such polysiloxane. Such substituents may include one or more elements, such as oxygen, nitrogen, carbon, hydrogen, halogen, sulfur, phosphorus, and the like and mixtures and combinations thereof.

Each $R^2$ preferably has 6 to about 10 carbon atoms. The substituents which may be included on the aryl ring include hydrocarbon substituents, such as alkyl groups, as well as other substantially non-interfering substituents, as described herein. In one particularly useful embodiment, $R^2$ is selected from the group consisting of aryl radicals. More preferably, each $R^2$ is phenyl.

Preferably, each $R^1$ radical is independently selected from divalent hydrocarbon radicals and divalent substituted hydrocarbon radicals, more preferably having 1 to about 6 carbon atoms. The substituents which may be included on $R^1$ are selected from substantially non-interfering substituents, as described herein. In a particularly useful embodiment, each $R^1$ is independently selected from alkylene radicals, more preferably from a methylene radical or an ethylene radical. In any event, it is important in the present invention that the aryl group or substituted aryl group, $R^2$, be separated or spaced apart from the silicon atom to which it is most directly bonded by 1 or more atoms. Without wishing to limit the invention to any particular theory of operation, it is believed that the presence of such a spacer group between the aryl group or substituted aryl group and the silicon atom to which it is most directly bonded provides the enhanced flexibility obtained in the present elastomeric compositions, while, at the same time, having little or no adverse effect on the enhanced refractive index achieved by incorporating such aryl-containing groups in the polysiloxane.

Each $R^3$ preferably has 2 to about 5 carbon atoms, and more preferably includes 1 carbon-carbon double bond. Each $R^3$ may be substituted with substantially non-interfering substituents, as described herein. More preferably, each $R^3$ is vinyl.

The present polysiloxanes may be produced by methods which comprise:

(a) contacting a cyclic hydride-containing siloxane monomer with at least one component having the formula $R^2$-f wherein $R^2$ is as described previously, and f is a functional monovalent radical capable of reacting with a silicon bonded hydride group of the cyclic hydride-containing siloxane monomer at conditions effective to chemically react the component with at least one of these hydride groups and form a cyclic aryl-containing siloxane monomer containing at least one —$R^1$—$R^2$ group wherein $R^1$ and $R^2$ are as described previously; and (b) contacting the cyclic aryl-containing siloxane monomer with at least one siloxane monomer at conditions effective to decyclize and polymerize the cyclic aryl-containing siloxane monomer, polymerize the siloxane monomer and form a polysiloxane having the following units

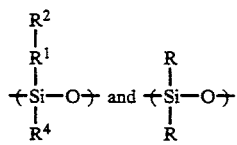

wherein each R and $R^4$ is independently selected as described above.

In another embodiment, methods for making polysiloxanes provide for a step (b) which comprises contacting the cyclic aryl-containing siloxane monomer at conditions effective to decyclize and polymerize the cyclic aryl-containing siloxane monomer and form a polysiloxane having a repeating unit of

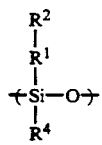

wherein each $R^4$ is independently selected as described above.

In many instances, at least one precursor of end blocking groups is included in step (b) and is reacted together with the other monomer or monomers present to form the end or terminal groups of the present polysiloxanes. Such precursors, for example, disiloxanes, are such to provide the $R^3$ groups to the present polysiloxanes. These precursors preferably include two terminal or end silicon atoms and an $R^3$ group bonded to each of the terminal silicon atoms. The precursor or precursors of end blocking groups are preferably included in step (b) in an amount effective to provide the polysiloxane formed with end blocking groups, such as described herein.

In step (a) of the above-noted methods, cyclic hydride-containing siloxane monomers are employed. Such monomers include three or more, preferably 3 to about 6, silicon atoms in a cyclic structure. Such monomers include at least one silicon bonded hydride group, i.e., Si—H. Preferably, two or more such hydride groups are included in the cyclic hydride-containing monomers. In a particularly useful embodiment, each of the silicon atoms of such cyclic monomers has at least one, and more preferably only one, hydride group directly bonded thereto. A number of useful cyclic hydride-containing siloxane monomers are commercially available. One especially useful such monomer is tetrahydrotetramethylcyclotetrasiloxane.

Step (a) of the present methods may comprise contacting the cyclic hydride-containing siloxane monomer or monomers with at least one component having a formula $R^2$-f where f includes a carbon-carbon multiple, preferably, double, bond at effective hydrosilation conditions.

The contacting at hydrosilation conditions may be catalyzed using, for example, one or more platinum group metal components, many of which are commercially available and conventionally used in vinyl/hydride addition curing of silicone polymers. The amount of platinum group metal, preferably platinum, component employed is effective to promote the desired hydrosilation in step (a). Such amount may be within the range of about 0.01 part per million (ppm) to about 100 ppm (or more) by weight of the total reactants present in step (a), calculated as elemental platinum group metal.

Step (a) may be conducted at hydrosilation conditions effective to provide the desired product. For example, temperatures in the range of about 10° C. or lower to about 60° C. or higher may be employed. Contacting times in the range of about 10 minutes to about 10 hours or longer have been found to be useful. Since the desired hydrosilation reaction of step (a) is often exothermic, the temperature of the reaction mixture may advantageously be controlled, e.g., by a cooling medium, to maintain the temperature in the desired range.

Alternately, step (a) can be accomplished using a Grignard-type reaction. In such a reaction, each component $R^2$-f is in the form of a so called Grignard reagent, the preparation of which is well known in the art. In this embodiment, step (a) may comprise contacting the cyclic hydride-containing siloxane monomer with a component such a Grignard reagent at effective Grignard reaction conditions to produce the desired cyclic aryl-containing siloxane monomer. Such Grignard reaction conditions include, for example, reaction temperatures in the range of about —60° C. or lower to about 0° C. or higher; and reaction times in the range of about 10 minutes to about 10 hours or longer.

The cyclic aryl-containing siloxane monomers alone or with other siloxane monomers, and preferably with precursors of end blocking groups, are reacted in the presence of a suitable catalyst to achieve decyclization and polymerization to the desired degree. The reactions can be conducted by using one or more of a variety of catalysts. Many such catalysts are well known in the art of cyclic siloxane polymerization. Examples of such catalysts include potassium hydroxide, tetramethyl ammonium hydroxide, derivatives thereof and mixtures thereof.

The amount of catalyst used in and the conditions at which step (b) occurs may be similar to those parameters which are conventionally employed in decyclizing and polymerizing other cyclic siloxane monomers. For example, the amount of catalyst employed may be in the range of about 0.01% to about 1% by weight of the total reactants. Temperatures in the range of about 20° C. to about 150° C. and reaction times in the range of about 0.5 hours to about 6 hours or more may be employed.

The degree of polymerization in step (b) is preferably monitored by monitoring the viscosity of the reaction mixture.

After the desired level or degree of polymerization is achieved, the catalyst is inactivated, neutralized, or removed, and the reaction product may be filtered.

After filtration, volatile materials are removed from the polysiloxane, for example, by repeated vacuum stripping.

The present elastomeric compositions comprise a cross-linked copolymer of (1) a polysiloxane having a formula as noted above and (2) a cross-linker component. Such elastomeric compositions preferably further comprise a reinforcer component in an amount effective to increase the strength of the composition. Preferably the present elastomeric compositions are optically clear and have a refractive index of at least about 1.46, more preferably at least about 1.48 and still more preferably at least about 1.50. Additionally, the present elastomeric compositions preferably have a combination of other properties, such as substantial flexibility, elongation and tensile strength, to provide optics for IOLs which are foldable and insertable through surgical incisions on the order of about 3 mm.

Particularly useful cross-linker components are selected from polyorganohydrosiloxanes and mixtures thereof. Many such polyorganohydrosiloxanes are commercially available and/or well known in the art for providing vinyl/hydride addition cure silicone polymers. In order to obtain enhanced compatibility between the polysiloxane and the cross-linker component and and/or enhanced refractive index of the elastomeric material, it is preferred that the cross-linker component have a refractive index which is substantially the same, for example, within about 0.05 and preferably within about 0.02, as the refractive index of the polysiloxane. Examples of particularly useful cross-linker components include copolymers of methylhydrosiloxane and phenylmethylsiloxane, copolymers of methylhydrosiloxane and diphenylsiloxane, and mixtures thereof.

The elastomeric compositions of the present invention preferably contain at least one reinforcer component dispersed in the elastomer composition.

In accordance with one embodiment of the invention, the reinforcer component is preferably used in a ratio of about 1 to about 45 parts by weight of the reinforcer component to 100 parts of the total elastomeric composition. Silica, preferably fume silica, and organic resins are very useful as the reinforcer component. Fume silica itself is commercially available. Processes for trimethylsilylating the surface of fume silica for the purpose of rendering the silica surface hydrophobic and more compatible with polysiloxane polymers are also known and within the skill of the art. A number of organic resins are known to be useful for reinforcing articles which include silicone elastomers. Of course, the reinforcer component used in the present elastomeric compositions employed in optical applications should be optically clear or at least have no significant detrimental effect on the optical clarity of the elastomeric composition. The refractive index of the reinforcer component is preferably at least about equal to or greater than the refractive index of the silicone elastomer in the elastomeric composition.

The fume silica reinforcer useful in the present compositions preferably has a surface area of about 100 to about 450 meters$^2$/gram.

In the preparation of the present elastomeric compositions, the polysiloxane is preferably intimately mixed with the reinforcer component. The intimate mixing is preferably aided by treating the mixture on a roll mill or like device. After intimate mixing, additional volatiles may be removed from the mixture by heat and vacuum.

This intimate mixture of polysiloxane and reinforcer component is hereinafter referred to as the "base". For the purpose of making materials suitable for use in IOLs, the base may be dispersed in a suitable inert solvent, such as trichlorotrifluoroethane (FREON), and the dispersion filtered to remove any solid impurities. Thereafter, the solvent is removed by gentle heat and vacuum.

The base preferably has the inherent characteristic of providing, after suitable curing by cross-linking, an elastomeric composition having physical properties which are highly advantageous for inclusion in a foldable IOL. Thus, after the curing or cross-linking step, the properties of the resulting cross-linked elastomeric composition preferably include in accordance with the present invention the following:

- an optical refractive index which is at least about 1.46, more preferably at least about 1.48 and still more preferably at least about 1.50;
- a Shore A durometer hardness value of at least about 25;
- a tensile strength of at least about 400 psi;
- a tear strength of at least about 20 pounds per lineal inch (pli); and
- an elongation of at about 100%, preferably at least about 200%.

The above listed properties can be measured in accordance with state-of-the-art technology and instruments in accordance with the respective requirements of standard ASTM test methods. More particularly, the durometer test is performed as ASTM D2240, the tensile and elongation tests as ASTM D412 and the tear strength test as ASTM D624 Die B.

In one embodiment, the durometer hardness is about 38 to about 40, the tensile strength is in the range of about 700 to about 750 psi, and the tear strength is about 40 pli. In this regard it is noted that cross-linking tends to slightly increase the optical refractive index as compared to the uncured base.

Preparation of the uncured base for cross-linking is preferably accomplished as follows. The base is divided into two aliquots which preferably are of equal weight. The aliquots are termed "Part A" and "Part B" or first and second aliquot parts. Cross-linking may be accomplished by utilizing a platinum group metal catalyzed reaction of the terminal silicon bonded multiple bonds (vinyl groups) of the base, and silicon bonded hydrogens or hydride groups of the cross-linking agent. The silicon bonded multiple bonds (vinyl groups) are present in both the first and second aliquots of the base.

Silicon bonded hydrogens or hydride groups are added in the practice of the present invention to the second aliquot (Part B) in the form of one or more suitable cross-linking agents, such as a polyorganohydrogen siloxane. The cross-linking agents per se are known in the art, and may be made in accordance with the teachings of U.S. Pat. No. 3,436,366, which is incorporated in its entirety herein by reference.

The platinum group metal, preferably platinum, catalyst can be selected from such catalysts which are conventional and well known in the art. Suitable catalysts include organo platinum group metal, preferably platinum, compounds, for example, in accordance with U.S. Pat. Nos. 2,823,218 and 3,159,601, each of which is incorporated in its entirety herein by reference. The catalyst may be added to the first aliquot (Part A).

After mixing of the aliquots (Part A and Part B), the cross-linking preferably should not proceed too rapidly at room temperature, thereby allowing at least about 2, more preferably at least about 4 or about 6, hours for work time with the mixed aliquots. For this reason, a suitable cross-linking inhibitor, such as 1, 2, 3, 4 tetramethyl- 1,2,3,4-tetravinyl cyclotetrasiloxane, is preferably added to the second aliquot (Part B).

The platinum group metal catalyst is present in the first aliquot in an amount in the range of about 1 ppm to about 50 ppm by weight. The cross-linker is preferably included in the second aliquot in an amount in the range of about 0.5 or about 1 to about 6 or about 10 parts per hundred by weight. The cross-linking inhibitor is preferably added to the second aliquot in an amount in the range of about 0.01 to about 0.2 parts per hundred by weight.

An ultraviolet light absorbing material, preferably a polymerizable ultraviolet light absorbing material, may be mixed into the second aliquot.

The ultraviolet light absorbing material, for example, selected from vinyl functional 2-hydroxybenzophenones and vinyl functional benzotrizoles, is preferably covalently linked to the silicone elastomer of the elastomeric composition during the cross-linking step. The ultraviolet light absorbing material is preferably added to the second aliquot in an amount in the range of about 0.1% to about 1% or about 5% by weight. The curing or cross-linking occurs at conditions effective to provide the desired elastomeric composition. Curing temperatures may vary, for example, from about 20° C. to about 200° C., and curing times may range, for example, from about 1 minute to about 5 hours or about 10 hours or more.

Formation of IOL bodies or optics from the elastomeric compositions of the present invention may be accomplished by liquid injection molding or by cast or compression molding or other types of molding of the intimately mixed first and second aliquots. These processes are well known in the art.

The following non-limiting examples illustrate certain aspects of the present invention.

EXAMPLE 1

24 g of tetramethylhydrocyclotetrasiloxane (from Petrarch System, Inc.) is added dropwise into a 25 g toluene solution containing 25 g styrene (Aldrich Chemical Company) and 1 ml platinum complex solution (Petrarch System, Inc.). The reaction is exothermal and is controlled at 40° C. using an ice bath. After complete addition of the tetramethylhydrocyclotetrasiloxane in 30 minutes, the reaction temperature is slowly raised from 40° to 75° C. in one hour and is maintained at 75° C. for another hour. The toluene solvent and unreacted styrene is removed by vacuum distillation. After the volatiles are removed, the product flask is found to contain 34 g of tetramethylstyrylcyclotetrasiloxane.

"H-NMR analysis indicates that alpha and beta substitutions have a ratio of about 1 to 1.6 and are as shown in the chemical structure illustrated below. The tetramethylstyrylcyclotetrasiloxane monomer has a refractive index of 1.53.

The above described reaction is illustrated as follows:

EXAMPLE 2

In a 2 liter reactor, tetramethylstyrylcyclotetrasiloxane (1088 g) and 1, 2 divinyltetramethyldisiloxane (6 g) are mixed and heated with agitation under a nitrogen gas blanket to 100° C. When the temperature reaches 100° C., 0.18 per cent (by weight) N-catalyst (tetramethyl ammonia hydroxide) is added. Stirring and heating are continued and the viscosity of samples taken from the reaction mixture is monitored. If after 45 minutes there is no change in viscosity, an additional 0.09 percent N-catalyst is added. After heating and stirring for another 3 hours, the catalyst is destroyed by heating the mixture to 150° C. The viscosity of the cooled reaction mixture should be between 2000 and 2800 cp. The refractive index should be between 1.52 and 1.54.

The polymer is stripped three times on a wipe film evaporator. The viscosity of the stripped polymer should be between 4100 and 5300 cp, and the refractive index should be between 1.53 and 1.54. This polymer is a vinyl terminated methylstyrylpolysiloxane.

EXAMPLE 3

The stripped polymer from Example 2 is passed through a 325 mesh steel wire screen under pressure. The batch is divided into two equal parts, Part A and Part B. 12 parts per million by weight of the organoplatinum catalyst identified in Example 1 is mixed into Part A. Small samples from Part B are mixed with various concentrations of a cross-linker, a liquid organohydrogen polysiloxane having a refractive index of 1.50 and sold by Petrarch Systems under the trademark PS 12905. The cross-linker level is optimized so as to obtain a Shore durometer hardness of approximately 25 or higher (ASTM D2240) in the cross-linked product. Thereafter, increasing amounts of an inhibitor (1,2,3,4 tetramethyl-1,2,3,4-tetravinylcyclotetrasiloxane are added to Part B and mixed samples of Parts A and B are tested to obtain a working time of about 6 hours or longer at room temperature. Depending on the above-noted sample test results, the cross-linker is added to Part B to provide 1-6 parts per hundred by weight, and the inhibitor is added to Part B to provide 0.01 to 0.2 parts per hundred by weight.

An elastomer prepared by curing equal amounts of Parts A and B (with 6 parts by weight of cross-linker at 100° C. for 30 minutes) has a refractive index of about 1.54 and sufficient tensile strength, elongation and tear strength to be useful for making foldable IOLs.

The physical properties of the cured elastomer can be further improved by adding silica gel or resin reinforcing agents into the formulation. Such reinforced elastomeric compositions are very useful for making foldable IOLs.

While this invention has been described with respect to various specific examples and embodiments, it is to be understood that the invention is not limited thereto and that it can be variously practiced within the scope of the following claims.

What is claimed is:

1. A method for making a polysiloxane comprising:
   (a) contacting a cyclic silicon bonded hydride-containing siloxane monomer with at least one component having the formula:

$R^2$-f wherein $R^2$ is selected from the group consisting of aryl radicals and substituted aryl radicals, and f is a functional monovalent radical capable of reacting with a silicon bonded hydride group of said cyclic silicon bonded hydride-containing siloxane monomer at conditions to chemically react said component with at least one of said silicon bonded hydride groups of said cyclic silicon bonded hydride-containing siloxane monomer and form a cyclic aryl-containing siloxane monomer including at least one —$R^1$—$R^2$ group wherein $R^1$ is selected from the group consisting of divalent radicals;
   (b) contacting said cyclic aryl-containing siloxane monomer with at least one other siloxane monomer and an effective amount of at least one end blocking group precursor at conditions effective to decyclize and polymerize said cyclic aryl-containing siloxane monomer, react said other siloxane monomer and form a polysiloxane having a refractive index of at least 1.46, end blocking groups derived from said at least one end blocking group precursor are radicals selected from the group consisting of monovalent hydrocarbon radicals having a multiple bond and substituted monovalent hydrocarbon radicals having a multiple bond, and wherein said polysiloxane has the following units:

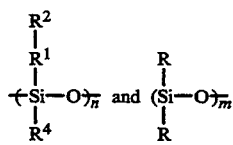

wherein each R and $R^4$ is independently selected from the group consisting of alkyl radicals, substituted alkyl radicals, aryl radicals and substituted aryl radicals, n is an integer in the range of 6 to about 500, m is an integer in the range of 1 to about 500, and the aryl-containing substituents in said polysiloxane comprise at least 10 mol % of the total silicon-bound substituents in said polysiloxane;
   (c) contacting said polysiloxane with at least one cross-linker component to form a cross-linked copolymer which is optically clear and has a refractive index of at least 1.46; and
   (d) forming a lens body for use in or on a mammalian eye including said cross-linked copolymer.

2. The method of claim 1 wherein each R has 1 to about 3 carbon atoms; each $R^2$ has 6 to about 10 carbon atoms; and each $R^4$ is independently selected from the group consisting of alkyl radicals and substituted alkyl radicals.

3. The method of claim 1 wherein each R and $R^4$ is methyl, each $R^1$ has 1 to about 6 carbon atoms, and each $R^2$ is phenyl.

4. The method of claim 1 wherein said end blocking groups are vinyl radicals and said polysiloxane has a refractive index of at least 1.48.

5. The method of claim 1 wherein said cyclic silicon bonded hydride-containing siloxane monomer has a plurality of silicon bonded hydride groups, and step (a) is effective to chemically react said component with all of said silicone bonded hydride groups of said cyclic silicon bonded hydride-containing siloxane monomer.

6. The method of claim 1 wherein $R^1$ is selected from the group consisting of methylene radical and ethylene radical.

7. The method of claim 1 wherein said polysiloxane has a refractive index of at least 1.50.

8. A method for making a lens body for use in or on a mammalian eye comprising:
   (a) contacting a cyclic silicon bonded hydride-containing siloxane monomer with at least one component having the formula $R^2$-f wherein $R^2$ is selected from the group consisting of aryl radicals and substituted aryl radicals and f is a functional monovalent radical capable of reacting with a silicon bonded hydride group of said cyclic silicon bonded hydride-containing siloxane monomer at conditions effective to chemically react said component with at least one of said silicon bonded hydride groups of said cyclic silicon bonded hydride-containing siloxane monomer and form a cyclic aryl-containing siloxane monomer including at least one —$R^1$—$R^2$ group wherein $R^1$ is selected from the group consisting of divalent radicals;
   (b) contacting said cyclic aryl-containing siloxane monomer with an effective amount of at least one end blocking group precursor at conditions effective to decyclize and polymerize said cyclic aryl-containing siloxane monomer and form a polysiloxane having a refractive index of at least 1.46, end blocking groups derived from said at least one end blocking group precursor are radicals selected from the group consisting of monovalent hydrocarbon radicals having a multiple bond and substituted monovalent hydrocarbon radicals having a multiple bond, and wherein said polysiloxane has a repeating unit of

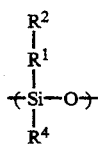

wherein each $R^4$ is independently selected from the group consisting of alkyl radicals, substituted alkyl radicals, aryl radicals and substituted aryl radicals;

(c) contacting said polysiloxane with at least one cross-linker component to form a cross-linked copolymer which is optically clear and has a refractive index of at least 1.4; and (d) forming a lens body for use in or on a mammalian eye including said cross-linked copolymer.

9. The method of claim 8 wherein each $R^4$ has 1 to about 3 carbon atoms and each $R^2$ has 6 to about 10 carbon atoms.

10. The method of claim 8 wherein each $R^4$ is methyl, each $R^1$ has 1 to about 6 carbon atoms, and each $R^2$ is phenyl.

11. The method of claim 8 wherein said end blocking groups are vinyl radicals and said polysiloxane has a refractive index of at least 1.48.

12. The method of claim 8 wherein said cyclic silicon bonded hydride-containing siloxane monomer has a plurality of silicon bonded hydride groups, and step (a) is effective to chemically react said component with all of said silicon bonded hydride groups of said cyclic silicon bonded hydride-containing siloxane monomer.

13. The method of claim 8 wherein $R^1$ is selected from the group consisting of methylene radical and ethylene radical.

14. The method of claim 8 wherein said polysiloxane has a refractive index of at least about 1.50.

15. The method of claim 8 wherein said cross-linked copolymer is elastomeric, and said lens body is the optic of an intraocular lens.

16. The method of claim 8 wherein step (c) occurs in the presence of an effective amount of a platinum group metal-containing catalyst.

17. The method of claim 8 wherein the aryl-containing substituents in said polysiloxane comprise at least 10 mol % of the total silicon-bound substituents in said polysiloxane.

18. The method of claim 8 wherein the aryl-containing substituents in said polysiloxane comprise at least about 20 mol % of the total silicon-bound substituents in said polysiloxane.

* * * * *